United States Patent [19]

Rooks

[11] Patent Number: 4,536,403

[45] Date of Patent: Aug. 20, 1985

[54] METHOD FOR TREATING NEUROLEPTIC INDUCED TARDIVE DYSKINESIA

[76] Inventor: J. F. Girard Rooks, 3181 Prairie St., P.O. Box 303, Grandville, Mich. 49418

[21] Appl. No.: 617,774

[22] Filed: Jun. 6, 1984

[51] Int. Cl.³ .............................................. A61U 31/27
[52] U.S. Cl. .................................... 514/483; 514/479
[58] Field of Search ........................................ 424/300

Primary Examiner—Stanley J. Friedman
Attorney, Agent, or Firm—Flynn, Thiel, Boutell & Tanis

[57] ABSTRACT

The involuntary movements associated with tardive dyskinesia induced by neuroleptic drug treatments are mitigated by administration of carisoprodol, a compound previously known only as a sedative and muscle relaxant.

6 Claims, No Drawings

METHOD FOR TREATING NEUROLEPTIC INDUCED TARDIVE DYSKINESIA

The present invention concerns a new therapeutic use of carisoprodol (N-isopropyl-2-methyl-2-propyl-1,3-propanediol dicarbamate) for the treatment of tardive dyskinesia associated with psychiatric treatments using neuroleptic drugs.

Tardive dyskinesia is an undesirable, but frequent, side effect of psychiatric treatments with neuroleptic drugs. The prevalence of and possible mechanism for tardive dyskinesia are discussed in *J. Clin. Psychiatry*, 40:508–516 and 41:427–428. Almost all antipsychotic drugs currently used in the United States exert undesirable neurological side effects. Such drugs are collectively referred to as neuroleptic drugs. Tardive dyskinesia is characterized by irregular involuntary movements of various parts of the body. The movements may be almost imperceptible, or may be so severe as to cause severe grimacing, thrusting and twisting movements of the torso, and thrashing movements of the head and limbs, respiratory movements, and movements of the tongue and jaw. The movements may develop during the course of treatment with one or more neuroleptic drugs, or may not become apparent until there is a reduction in dosage, change of medicine or interruption in treatment. Dyskinesias developing during the reduction in dose of neuroleptic drugs, or shortly following their discontinuance are sometimes referred to as withdrawal dyskinesias. Withdrawal dyskinesias are a sub-type of tardive dyskinesia, for the purposes of this application, as are tardive dystonias. Tardive dystonias are neuromuscular reactions resulting in sustained abnormal postures, such as of the hand, fingers or head, which develop sometime after the discontinuance of neuroleptics.

No effective acceptable treatment for tardive dyskinesia has been reported. Recent research has focused mainly on preventing tardive dyskinesia by finding antipsychotic drugs which are not neuroleptic, as described in *Tardive Dyskinesia: Summary of a Task Force of the American Psychiatric Association*, Am J Psychiatry 137:10, October 1980, p. 1163–1172. A variety of drugs have been tried for the treatment of tardive dyskinesia, with little success. As described in the foregoing Task Force report, agents which may partially suppress tardive dyskinesia include dopamine antagonists, amine-depleting agents, blockers of catecholamine synthesis, blockers of catecholamine release, and cholinergic agents, specifically including apomorphine, butyrophenones, clozapine, papaverine, phenothiazines, pimozide, reserpine, tetrabenazine, alphamethyldopa, alpha-methyltyrosine, lithium salts, deanol, choline and lecithin, physostigmine, baclofen, valproate, and muscimol. In general, tranquilizers and muscle relaxants have been found ineffective for treating tardive dyskinesia. The use of dopamine blocking antipsychotic drugs, such as thioridazine, for the control of the movements of tardive dyskinesia, has been described, however these treatments involve the further use of drugs which are known to cause and aggravate tardive dyskinesia, in chronic use, apparently through their dopamine blocking action.

Carisoprodol is significantly different as a treatment for tardive dyskinesia, from all of the drugs currently considered to provide measurable symptom reduction, in that the other drugs (reserpine and antipsychotic neuroleptic drugs) appear to suppress these symptoms by dopamine blockade or depletion, which is believed to be the mechanism by which tardive dyskinesia is caused, whereas carisoprodol does not have this mechanism of action.

The present invention is directed to a method for treating tardive dyskinesia using carisoprodol, that is, N-isopropyl-2-methyl-2-propyl-1,3-propanediol dicarbamate, a prescription medication which is reported to rapidly produce muscle relaxation by blocking interneuronal activity in the descending reticular formation and spinal cord. The present inventor has discovered that carisoprodol produces a significant degree of reduction of and relief from the abnormal movements associated with tardive dyskinesia induced by a wide variety of neuroleptic drugs. Carisoprodol is also known as (1-methylethyl)carbamic acid 2-[[(aminocarbonyl)oxy]methyl]-2-methylpentyl ester, isopropyl meprobamate, isobamate, and carisoprodate. The preparation of carisoprodol is described in U.S. Pat. No. 2,937,119, the contents of which are hereby expressly incorporated by reference into the present application.

Carisoprodol has been previously used as a skeletal muscle relaxant having sedative properties. Muscle relaxants and sedatives have generally not been found useful for the treatment of tardive dyskinesia. As to the toxicity of carisoprodol, Berger et al, J. Pharmacol. Exp. Ther., 127, 66 (1959) reported that $LD_{50}$ in mice equals 2340 mg/kg orally and 980 mg/kg i.p., and in rats $LD_{50}$ equals 1320 mg/kg orally and 450 mg/kg i.p. The principal adverse side effect of carisoprodol is sedation during treatment. A variety of uncommon but more severe adverse effects of the first dose of carisoprodol are also known. Such initial adverse effects generally subside a few hours after the treatment is initiated but may continue in milder form throughout the treatment.

According to the method of the present invention, a human patient suffering from tardive dyskinesia is administered internally with a therapeutically effective dosage of carisoprodol. The dosage used is not critical and can be any amount which is effective to mitigate or eliminate the symptoms of tardive dyskinesia in the particular patient involved. Carisoprodol is preferably administered orally in the form of tablets. The current, commercially available tablets generally contain 350 mg of carisoprodol per tablet. A dosage amount of carisoprodol in the range of from 100 to 2200 mg/day for a human adult is preferred, and a dosage range of 350–1050 mg/day per adult is particularly preferred. The dosage of carisoprodol generally employed for muscle relaxant purposes is 1500 mg/day per adult, but the effects against tardive dyskinesia according to the present invention often can be obtained with a lower dosage range as noted above. If the patient suffering from tardive dyskinesia is a child, the foregoing dosage ranges should be adjusted downwardly.

The patient can concurrently undergo treatment for a psychiatric condition using one or more neuroleptic drugs, that is, the patient may be taking one or more of the neuroleptic drugs which induced the tardive dyskinesia, at the same time as he receives carisoprodol for treatment of the tardive dyskinesia. Carisoprodol is compatible with most known neuroleptic antipsychotic drugs. In particular, carisoprodol can be taken concurrently with at least the following neuroleptic drugs: fluphenazine, haloperidol, mesoridazine besylate, perphenazine, thioridazine, thiothixene, and trifluoperazine; benzodiazepines, such as chlorazepate; tricyclic antidepressants; and maprotiline; antiparkinson drugs, such as benztropine mesylate, and various combinations of these drugs. In addition, carisoprodol can be administered to a patient suffering from tardive dyskinesia, but who is no longer taking neuroleptic drugs.

The present invention is based on the following experimental results. In the examples, the patients treated were outpatients and most were receiving psychiatric treatment through a community mental health system. All had received antipsychotic neuroleptic drugs for a period of years, and all had developed irregular involuntary movement disorders while receiving such drugs, or very shortly after discontinuing use of such drugs. Most of the test patients continued to use neuroleptic drugs during the carisoprodol treatments.

The following seven patients are discussed in the order in which they were treated. These patients served as their own controls. In addition, a simple placebo-controlled blind study was carried out involving three additional patients.

EXAMPLES

Patient 1. Initial Observation.

An intelligent 43 year old pre-menopausal woman with a diagnosis of chronic undifferentiated schizophrenia with persistent paranoid delusions, whose symptoms could not be controlled with lithium carbonate (to a serum lithium level of 0.9), and whose neuroleptic treatment of 32 mg to 64 mg of perphenazine daily was accompanied by 1 mg to 4 mg daily of Cogentin ® (Benztropine mesylate, M.S.D.), and who had been observed over a 21 month period to have developed involuntary irregular twitching movements of her thumb and fingers, then occasional restless movements of her feet, then occasional extension movements of the fingers of her left hand, then an urge to chew all the time and dorsi-flexion movements of her crossed foot (but no buccal, labial, or lingual movements, even with efforts at augmentation), reported that the movements suggestive of tardive dyskinesia had not been noticed during a 3 month period of treatment with Soma Compound ® (carisoprodol, phenacetin, and caffeine). Soma Compound has been reformulated since this study was conducted and now contains only carisoprodol and aspirin. Later, she ran out of the Soma Compound and the twitching movements returned to her fingers after about 16 hours. At that time she also reported feeling some movement under the skin of her face, but had not been able to observe it in a mirror. She was then given carisoprodol 350 mg twice daily and the movements in her hands, fingers and feet ceased. She continued to receive perphenazine (generally at a dose of 40 mg daily), Cogentin 1 mg daily, and carisoprodol 350 mg morning and evening and 175 mg in the afternoon. She has used carisoprodol continuously for 16 months with continued relief from undesirable movements and without apparent adverse effect. The only apparent side effects were transient mild nausea and transient mild sedation.

Subsequent Patient Selection.

Following this patient's first report of relief from her movement disorder, six more patients with neuroleptic induced tardive dyskinesia were briefly treated with carisoprodol.

Patient 2.

A 59 year old woman with diagnoses of residual schizophrenia, hypothyroidism, chronic headaches and chronic low back problems, who had been treated with perphenazine, thioridazine, Cogentin, tricyclics, and benzodiazepines, had developed movements of her tongue inside her closed mouth, lip and jaw movements, an abnormal extension posture of her fifth finger and a stiff appearing (but not rigid) resting hand posture, eyelid retraction, chewing movements, and easily audible irregular exhalation sounds. During the next 13 months these movements continued and mild lip smacking and toe and finger movements developed. She complained of her muscles feeling tight.

With carisoprodol, 350 mg tablets administered twice a day, both the patient and her husband observed at least partial relief from all of the abnormal motor activity. After nine tablets, she stopped the carisoprodol because of frontal headaches. Headaches were a frequent complaint in connection with prior medicine changes, and an almost constant complaint since the carisoprodol was stopped.

Later, with carisoprodol, 350 mg each A.M., the exhalation and lip smacking sounds ceased and the other movements were relieved but to a lesser degree than with 350 mg twice a day. When carisoprodol was stopped, after 3 weeks of 350 mg each A.M., the finger movements, lip smacking, and exhalation sounds returned. Ten weeks later she experienced no subjective improvement from 350 mg daily but achieved partial relief with 350 mg twice a day, having decided on her own to use her remaining tablets.

This patient's underlying psychiatric condition has been controlled with maprotiline and clorazepate for the past sixteen months, and it is now considered likely that her psychosis is basically a cyclic affective disorder.

Patient 3.

A 40 year old woman with a 14 year history of paranoid schizophrenia, whose delusions continued in spite of treatment with various antipsychotic neuroleptics, developed involuntary tongue movements which disturbed her speech. On examination she was found to have difficulty maintaining her tongue in a steady protruded position. At rest, some movements of the tongue were visible. Irregular involuntary twisting tongue movements were observed as she spoke. Movements of the circum-oral muscles were present, and could be increased by augmentation. Dyskinetic finger movements and restless hand movements were also noted. This condition developed rather abruptly during treatment with molindone and Cogentin administered four times a day. The molindone was reduced from 100 mg daily to 25 mg administered every second day. Movements of the legs, feet, arms, hands, fingers, face and (questionably) the trunk were observed. These movements became minimal, but observable, within two months after the molindone dose was reduced. Oxazepam and chlordiazepoxide were used briefly to calm the patient, but psychotic symptoms required a return to more neuroleptic medicine and thioridazine was started.

After eight months of dyskinetic movements, the patient was given carisoprodol, 350 mg tablets each A.M., while receiving thioridazine 150 mg daily. Her previous occasional involuntary movements of the fingers and hands stopped, but she was sedated and sleepy. The carisoprodol 350 mg was then given only at bedtime, and the movements continued under control without daytime sedation. Subsequently, movement symptoms increased with a temporary increase to 200 mg daily of thioridazine, while carisoprodol 350 mg at bedtime was continued. The carisoprodol was stopped after the thioridazine was decreased again and movements did not return.

Patient 4.

A 30 year old woman with a long history of relatively mild chronic paranoid schizophrenia and intermittent mild depressions, who was treated with trifluoperazine, had developed a twitching movement of her left shoulder. While walking she had slight involuntary movements of her fingers and an athetoidtype of hand posture. Her child told her that she made "fish mouths" while driving her car. Thioridazine was given in place of the trifluoperazine and the movements continued in her left shoulder and left fifth finger, at rest. Her children continued to comment on her "fish mouth".

After eight months of these mild but definite movements carisoprodol, 350 mg tablets twice a day, was started. She complained of sedation which interfered somewhat with her work, but the movements were reported to be less frequent and "less quick". After six days, she stopped the carisoprodol and the movements became more pronounced and more frequent. Two weeks later she spontaneously returned to carisoprodol for four days, during which time she felt sleepy but, "my muscles felt more at ease" and the frequency and intensity of the movements was reduced. She then decided to use it as needed for social occasions.

Patient 5.

A 34 year old woman with chronic schizophrenia, treated with antipsychotic neuroleptics, was noted to have developed retraction of the corners of her mouth, quick irregular involuntary movements of her fingers and occasional jerky movements of her shoulders and upper arms. Carisoprodol, 350 mg tablets twice a day, seemed to reduce the movements, but there were problems in the scheduling of appointments to observe her. The dose was increased to 350 mg three times a day, with meals. After one week, she reported subjective improvement and was observed to have less frequent and less severe finger movements and no shoulder or arm movements.

The carisoprodol was stopped because of the development of a slight facial rash. She later expressed a preference for carisoprodol over thioridazine. Mild dyskinetic movements of the lips, extension movements of the fingers, and occasional movements of the head, shoulders, and feet continued to be observed, but not at every visit.

Patient 6.

A 61 year old man who had been diagnosed initially as having paranoid schizophrenia, but later was diagnosed as having bipolar affective disorder, was using haloperidol 20 mg daily and Cogentin 2 mg daily when he was observed to have involuntary movements of his tongue and lower lip. He stated, "I suck my lip", something he had never done previously. Under stress, he would abruptly, involuntarily, and irregularly flex his hip so that his foot would be lifted off the floor.

Four weeks later, while exhibiting labial movements, chewing movements, finger movements, and lip sucking, he was begun on carisoprodol, 350 mg twice a day. One week later, while denying sedation or any other side effects, he enthusiastically reported less movement and stated, "I've stopped sucking my lip". No movements of finger, arms, or lower extremities were noted. There was occasional very slight protrusion of the tongue against the lower lip, slight vermicular movement of the tongue at rest, and barely perceptible lateral movement of the jaw. He was then briefly lost to follow-up, ran out of carisoprodol, used his neuroleptics irregularly, and then returned irregularly for follow-up visits showing varying degrees of movements of his tongue, jaw, fingers, and hands, as well as lip sucking.

Patient 7.

A 41 year old woman with a history of twenty years of chronic undifferentiated schizophrenia and at least thirteen years of continuous hospitalization developed tardive dyskinesia after many years of treatment with thiothixene and Cogentin. Her abnormal movements began with slight twitching under her left eye and a few little twitches in the lower part of her face. Eyebrow raising movements and contractions at the right corner of her mouth developed over the next six months. To these movements were added stiff lateral masticatory jaw movements, wormlike movements of the right third, fourth and fifth fingers, increased blinking and squinting, and movements of the chin and lips.

After more than two years of observed abnormal movements, an attempt was made to treat her with carisoprodol, but she discarded the medicine, having been alarmed by a description of the rarely reported, severe side effects. She was very skeptical of requests for brief, frequent appointments. Compliance with continued efforts to initiate this trial of treatment was questionable, and initial observations revealed no obvious change in the movements. On one occasion when the care giver was sure that carisoprodol had been taken a few hours earlier, the movements of her face were minimal and the finger movements were reduced. She did not appear sedated at this time. A later effort to reduce the movements with carisoprodol failed, but reliability of carisoprodol ingestion was somewhat in doubt at the time reliable observations were made.

Placebo Controlled Double Blind Study

The Method.

Twenty different possible movement or postural effects of tardive dyskinesia were rated on a scale of zero to four:

0=not observed
1=trace-questionable
2=mild but definite
3=moderate
4=severe

Observations were made prior to treatment, one hour after the first dose of each medication and on the third or fourth day of treatment when the patient had used two or three doses earlier in the day.

Patients were instructed to use one tablet the first day, two the second, three the third, and four on the fourth day. Each phase of treatment was concluded prior to use of the last pill on the fourth day.

Efforts were made to expose and exaggerate the movements by means of augmentation. Movements were recorded in the most severe category for which they qualified. Each patient was accompanied by a family member or other care giver, and these persons were instructed in recording the movements, and kept daily observations throughout the study. Patients were questioned closely regarding subjective impressions and observations. Pyridoxine H Cl 100 mg tablets were used as the placebo. Carisoprodol was administered as 350 mg tablets.

The Results.

Patient 1.

A twenty year old chronically manic, epileptic woman, six months post partum, who had earlier been diagnosed as suffering from schizo-affective schizophrenia, was first noted to have a movement disorder one week after discontinuing mesoridazine besylate, which had been reduced from a 500 mg daily dose during the preceding two months. She had lived independently, and used her medicines somewhat irregularly until two days before her movement symptoms were observed. During the study she lived in adult foster care.

Her movement disorder was severe and progressed over a two or three week period until she was having violent, sudden, uncontrollable, wide amplitude tossing movements of her head in all directions, severe twisting movements of her trunk when standing, severe arm movements for which she held her arms clutched around her chest, severe movements of her eyebrows and forehead, and movements of her lips, hands, fingers, shoulders, legs and jaw.

No improvement was observed on placebo and her movement score went from 26 to 30, because severe leg movements were observed at the final placebo rating. After four days with neither drug, the pre-treatment score was 35. Eighty-five minutes after the first dose of carisoprodol the movement score was 20. On the third day of carisoprodol the score was 16. Four days after the carisoprodol was stopped, the movement score was 38.

On placebo the patient was "a little sleepy" but reported no improvement. On carisoprodol the patient reported "I'm a lot better, I think". No side effects were present. On carisoprodol, the observed movements were less frequent, of smaller amplitude and were causing less social and ambulatory impairment. The patient appeared more comfortable.

The foster care employee rated the pre-treatment and placebo movements at 26 and 27, while rating the carisoprodol movements at 18. Surprisingly, this employee denied having observed any change, and still rated the movements at 18 four days after carisoprodol had been stopped. In spite of this, an emergency call was received the following day because the patient's movements had caused the breaking of a lot of dishes, and three employees complained that the movements had been much worse since the carisoprodol was stopped.

Patient 2.

A 32 year old man with a diagnosis of schizophrenia reported that his tardive dyskinesia had begun six years earlier when fluphenazine injections were started. The injections were continued and the movements were thought not to have increased in severity. The patient denied having, or ever having had a psychiatric illness. He appeared a bit suspicious of the study.

His movements consisted of mild lip and jaw movements, trace shoulder and body movements, moderate arm movements, moderate to severe finger movements and severely disturbed hand posture (both hands deviated to the left) which was increased while walking.

The pre-treatment score was 17. Ninety minutes after his first dose of carisoprodol the score was 13. On the fourth day his score was 16. The placebo score was 22. Ratings of the subject's behavior by his father ranged from 14 to 16 on carisoprodol and 13 to 21 on placebo. Ninety minutes after the first carisoprodol administration the patient stated, "It does feel a little less, but I'm not sure". On the fourth day of treatment he was unaware of any improvement or adverse effect.

On placebo the patient noted no change. His father thought he was worse on placebo than on carisoprodol.

The patient appeared to be more restless on placebo and the movements were easier to observe, and more frequent.

Patient 3.

A sixty year old man diagnosed as suffering from schizophrenia states that his movement disorder began after years of treatment with thioridazine. His family is more aware of his movements than he is. He had respiratory muscle involvement that was rated as "severe". Finger, tongue and lip movements were rated "moderate". Arm, cheek, chin, and jaw movements were "mild", and tongue protrusion was "trace". His pretreatment score was 22. One hour post-carisoprodol his score was 14. On the fourth treatment day it was rated twice. Initially it was 19, and after sitting for an hour it was 8. His placebo score was 22.

His wife thought he was sleepy on carisoprodol, but didn't notice any change in his movements, except that his breathing was more normal. He thought his tongue moved less, and he felt calmer: "I know I didn't make as much movement with my hands and I could sit still." He denied being sleepy, but acknowledged yawning more. He didn't feel any benefit on placebo, and noted that his tongue was moving more again.

The foregoing experimental results demonstrate that the movements of tardive dyskinesia spontaneously vary in intensity, are aggravated by arousal and physical activity, and apparently can subside during quiet relaxation. These factors complicate the evaluation of treatment induced changes in this condition. The results indicate that carisoprodol reduces the frequency and severity of the movements of tardive dyskinesia. The use of carisoprodol is likely to produce more obvious improvement when the movement disorder is more severe. While carisoprodol apparently did not relieve the movements of tardive dyskinesia in every patient, it should be noted that patient noncompliance was a factor when relief was not observed.

The beneficial effects of the carisoprodol treatments continued only as long as the carisoprodol administration was continued. In view of the wide variety of different neuroleptic drugs taken by the test patients, it may reasonably be concluded that carisoprodol is generally effective for treating tardive dyskinesia regardless of the particular neuroleptic drug or drugs responsible for causing the tardive dyskinesia. The method of the present invention is therefore of great value, particularly in relieving the tardive dyskinesia caused by antipsychotic drugs used for the treatment of conditions such as schizophrenia, paranoia, mania, depression, severe behavioral problems, drug induced psychosis, or psychosis resulting from some other cause.

The embodiments of the invention in which an exclusive property or privilege is claimed are defined as follows:

1. A method of treating tardive dyskinesia induced by treatments with a neuroleptic drug, which comprises orally administering internally to a human patient suffering from tardive dyskinesia a therapeutically effective amount of carisoprodol.

2. A method as claimed in claim 1, wherein the dosage of carisoprodol is in the range of 100–2200 mg/day.

3. A method as claimed in claim 2, wherein the dosage of carisoprodol is in the range of 350–1050 mg/day.

4. A method as claimed in claim 2, wherein said tardive dyskinesia was induced by treatment with at least one neuroleptic drug selected from the group consisting of perphenazine, thioridazine, trifluoperazine, haloperidol, thiothixene, fluphenazine, mesoridazine besylate, and combinations thereof.

5. A method according to claim 1, wherein said patient is further suffering from schizophrenia, mania, paranoia, depression, severe behavioral problems, drug induced psychosis, or non-drug induced psychotic condition.

6. A method as claimed in claim 2, wherein said tardive dyskinesia was induced by treatment with at least one neuroleptic drug selected from the group consisting of perphenazine, thioridazine, trifluoperazine, haloperidol, thiothixene, fluphenazine, mesoridazine besylate, prochlorperazine, loxapine, molindone, piperacetazine, chlorpromazine, triflupromazine, promethazine, tricyclic antidepressants, and therapeutically effective salts thereof.

* * * * *